United States Patent [19]

Lersmacher et al.

[11] 4,367,246
[45] Jan. 4, 1983

[54] METHODS OF MANUFACTURING CRUCIBLE FOR FLAMELESS ATOMIC ABSORPTION SPECTROSCOPY

[75] Inventors: Bernhard Lersmacher, Aachen, Fed. Rep. of Germany; Wilhelmus F. Knippenberg, Eindhoven, Netherlands

[73] Assignee: U.S. Philips Corporation, New York, N.Y.

[21] Appl. No.: 230,831

[22] Filed: Feb. 2, 1981

[30] Foreign Application Priority Data

Feb. 9, 1980 [DE] Fed. Rep. of Germany ....... 3004812

[51] Int. Cl.³ ............................................ G01N 21/16
[52] U.S. Cl. ..................................... 427/228; 427/230; 427/237; 427/249; 427/292; 427/309; 427/402
[58] Field of Search ............... 427/228, 249, 309, 230, 427/237, 292, 402; 356/312; 422/122

[56] References Cited

U.S. PATENT DOCUMENTS

| | | | |
|---|---|---|---|
| 3,819,279 | 6/1974 | Braun et al. | 356/244 |
| 3,854,979 | 12/1974 | Rossi | 427/228 |
| 3,936,535 | 2/1976 | Böder | 427/228 |
| 4,082,460 | 4/1978 | Braun et al. | 356/244 |
| 4,204,769 | 5/1980 | Lersmacher et al. | 356/312 |
| 4,293,512 | 10/1981 | Luhleich et al. | 427/249 |

*Primary Examiner*—John D. Smith
*Attorney, Agent, or Firm*—Paul R. Miller

[57] ABSTRACT

A preform made of carbon, and especially electrical graphite (electro-graphite), is given a protective coating of pyrolytic graphite which, in turn, is activated by further coating with a carbon with a very low degree of orientation (soot) or by roughening. The process of activation reduces the effect of the sample to be analysed, while the protective effect of the pyrolytic graphite coating is preserved.

4 Claims, 1 Drawing Figure

U.S. Patent  Jan. 4, 1983  4,367,246
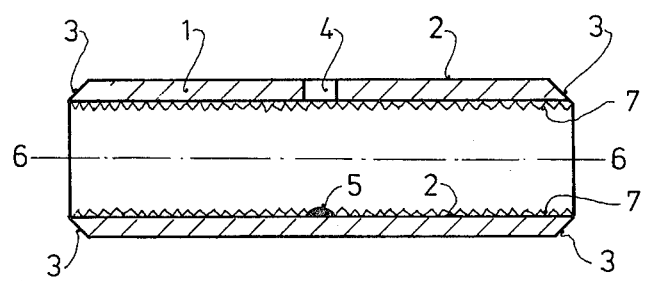

METHODS OF MANUFACTURING CRUCIBLE FOR FLAMELESS ATOMIC ABSORPTION SPECTROSCOPY

The invention relates to a crucible for flameless atomic absorption spectroscopy (AAS) of a sample, consisting of a carbon preform with a coating of pyrolytic graphite, and to a method of manufacturing it.

The crucible used in AAS are containers for the sample to be analysed. They can also be used as resistors, forming the resistance furnace for the electrical heating of a sample. They are generally tubular. They are made of carbon, especially graphite. For this purpose, electrographite, a highly pure polycrystalline material, provides a number of particular advantages. For example, electrographite has a high sublimation temperature (vapor pressure at 3000° C. of about 1.33 mbar), it is insensitive to abrupt changes of temperature, it has good chemical resistance and is very easy to machine. Moreover, electrographite is fairly cheap.

Its chemical resistance depends very largely on the temperatures and substances with which the graphite comes into interaction. There is, for instance, a marked reaction with oxygen and a number of metal oxides even at relatively low temperatures (from about 500° C.). This interaction is even further enhanced by the fact that polycrystalline electrographite is fairly porous, and thus provides a rather large area for chemical interactions, where the reactive centers are also affected by the crystallite size and distribution. Graphite may thus be regarded as a reducing agent, the activity of which increases greatly with the temperature. This reducing action may be favorable or unfavorable for AAS purposes, depending on the form taken by the elements in the sample for analysis.

German patent application No. 22 19 594, corresponding to U.S. Pat. No. 3,819,279 teaches the coating of the surfaces of AAS crucibles directed towards the sample with a protective layer of porous carbon. German patent application No. 22 25 421 proposes a heating element of a porous or foamed material, especially porous graphite or carbon, with current flowing through it, for heating purposes. In German patent specification No. 25 58 948, corresponding to U.S. Pat. No. 4,082,460 the outer envelope of crucibles is mechanically roughened at least in parts to provide better temperature measurement.

In addition, German patent application 27 02 189, corresponding to U.S. Pat. No. 4,204,769 teaches the provision of graphite crucibles with a protective coating of properly oriented pyrolytic graphite. This does indeed give the crucibles a markedly longer useful life and makes the measured values more easily reproducible. On the other hand, however, the aforementioned reducing action is weakened to a greater or lesser extent. This last-mentioned effect is caused by the crystallographic preferential orientation in pyrolytic graphite. The reduced reactivity is thus particularly noticeable in the lower and medium temperature ranges, i.e. up to about 1200° C.

Some reducing action at lower temperatures, too, may, however, be desirable. This is so if the elements to be detected are in the form of oxides which are more or less volatile. The best devices would therefore be an AAS crucible consisting of a pyrolytic-graphite-coated electrographite preform in which the pyrolytic graphite protective coating is still active enough as a reducing agent even at lower temperatures.

The aim of the research resulting in the invention was to give material form to the requirements of this kind of design, which are sometimes mutually exclusive. An inherently useful coating for AAS consisting of dense, impermeable pyrolytic graphite is, however, necessarily relative slow to react up to high temperatures.

It is thus the purpose of the invention to preserve the protective effect of such a coating, while at the same time increasing its reactivity as described above.

In an embodiment of the invention, this purpose is attained by mechanically or chemically roughening at least that part of the pyrolytic graphite layer which comes into contact with the sample.

In another embodiment of the invention, the purpose is attained by coating at least the pyrolytic graphite coating contacting the sample in the crucible with carbon having a very low degree of orientation and whose crystalline perfection differs greatly from that of the ideal graphite lattice.

The pyrolytic graphite coating is preferably coated with carbon by the physical or chemical deposition of the material from the gas phase. Here, care must be taken to control the deposition reaction in such a way that the degree of orientation of the deposited carbon is very low and its crystalline perfection differs greatly from that of the ideal graphite lattice.

In a preferred method of operation, the pyrolytic graphite layer is coated with an emulsion consisting of carbon or soot particles, a thermally decomposable emulsifier and a volatile solvent, whereafter the crucible is heated until the carbon or soot particles remain behind.

According to the invention a further surface coating of carbon with a considerably higher reactivity and thus a better reducing effect is provided on the protective layer consisting of properly oriented graphite. To do this, the surface is so shaped that as many reactive centers as possible can enter into interaction with the environment. In such reactive centers the proportion of crystallographic prismatic and pyramidal areas is as large as possible in relation to the base areas densely occupied by C atoms. This activated surface state is obtained in the invention by two means:

1. A particularly effective and simple method is the activation of the surface by mechanical or chemical roughening of the pyrolytic graphite protective layer on the AAS crucible. Mechanical roughening may, for instance, be effected by sandblasting or by machining with metal brushes, and chemical roughening by etching or anodising.

2. A preform coated with properly oriented pyrolytic graphite is given a further coating of carbon whose degree of orientation is as low as possible and whose crystalline perfection differs as greatly as possible from that of the ideal graphite lattice. An adherent soot coating, for instance, confers the required properties. A particularly good method of providing such an active carbon layer is chemical or physical vapour deposition from the gas phase (CVD and PVD processes), in much the same manner as used in the manufacture of carbon-film resistors. It is also possible to produce the sooty reactive coating by first introducing an emulsion into the crucible. The components of this emulsion must be such that they do not interfere with the analysis. A suitable emulsion of this kind, for example, contains cellulose or a cellulose derivative in a solvent and carbon particles or soot. When the crucible is used, the cellulose constituents are converted into carbon. This method has the advantage that it is easy to apply and the quantity of reactive carbon is substantially more variable than in the other two methods.

Although it is necessary in the method of the invention only to coat or roughen the part of the crucible, i.e. generally the inside, which comes into contact with the sample to be analysed, it is often simpler to subject the whole of the surface of the crucible to the treatment of the invention.

The AAS crucible of the invention is a kind of bonded component with a core, i.e. the preform of carbon, especially electrographite coating with a protective layer of highly oriented pyrolytic graphite, in turn activated by the further coating with a carbon layer with a very low degree of orientation (soot) or by roughening.

In a further embodiment of the invention, both methods are combined, whereby the crucibles are first roughened before the application of a second (active) carbon coating. This gives better adhesion than with a naturally grown coating of pyrolytic graphite.

The invention will be explained in greater detail with reference to a drawing and a few embodiments.

BRIEF DESCRIPTION OF THE DRAWING

The sole FIGURE shows a cross-section through an AAS crucible for horizontal operation.

The crucible consists of a preform 1 of electrographite, coated with an enveloping layer 2 of pyrolytic graphite. The ends of the crucible have contact surfaces 3. A hole 4 in the crucible wall is provided for loading the crucible with a sample 5. The measuring beam when the crucible is in use passes along line 6—6. The activated surface state of layer 2 is in the region of the crucible contacting sample 5, i.e. the roughening or the additional carbon coating.

EXAMPLE 1

The following method was used to investigate the effect of pyrolytic surfaces on crucibles: highly pure electrographite preforms were first coated with pyrolytic graphite (thickness 20 to 30 μm) in a known manner.

One pair of each of these crucibles was then:
(a) mechanically surface-roughened (inside and out) by sandblasting, or
(b) given a sooty carbon coating by the CFD process.

The crucibles, thus treated, were examined in an oxygen-containing atmosphere in specified conditions to test the activation. The results may be summarised as follows: At temperatures up to 1000° C., preferably at 860° C., the interaction between the activated carbon and the atmospheric oxygen is considerably increased; the reaction rates in time (about about 860° C.) are in the relation 1:8:12 (pyrolytic graphite to mechanically roughened pyrolytic graphite to soot-coated pyrolytic graphite). The electrical and heat conductivity of the activated crucibles is markedly lower, and the emission coefficient significantly higher. The oxidation rates of the activated carbon at 850° C. correspond roughly to those of pyrolytic graphite at 1100° C. These results clearly show that the reactivity of the activated carbon layer is markedly increased.

EXAMPLE 2

The surfaces of the crucibles were activated in a very neat manner: the coated crucibles, bedded in fine quartz sand like that used for sand-blasting, were rotated in a drum on a lathe. In addition, a number of pyrolytic-graphite-coated crucibles were put into a wide-necked polyethylene flash which was then roughly half-filled with fine-grained grinding powder and the whole rotated for a given time on the lathe.

This method has the following highly significant advantages:
(a) very simple operation;
(b) accurately measurable removal or roughening by adjusting the treatment time, and also possibly by the choice of grinding powder, e.g. fine-grained SiC;
(c) uniform removal.

The table below gives results of test made on the lathe.

TABLE

| Rotation time in min. | Weight reduction in mg | Average coating thickness reduction in μm |
|---|---|---|
| 15 | 0.5 | 0.2 |
| 60 | 1.7 | 0.7 |
| 120 | 2.5 | 1.0 |

These data are based on the assumption of uniform removal inside and out. It is certain that this assumption must be corrected, since the removal on the outside seems greater. Such a conclusion is also indicated by the tests made to determine the increase in the activity. The results of oxidation tests may be summarised as follows:

All the crucibles treated in accordance with the invention show increased tendencies to oxidise in the 700° to 1000° C. range as compared with untreated crucibles. The reaction rate is greater by factors of some 3 to 10 (reaction equation: $C+O_2 \rightarrow CO_2$). The selected test reaction can no longer be used above 1000° C.

Roughening provides advantages only if it affects only the outer surface regions of the pyrolytic graphite, in the range 0.1 to 1.0 μm. Removal of more material provides no further gain. This result agrees fully with the behavior to be expected from the structure, according to which a heavier material removal invariably reveals only areas of the "same reaction potential". Only if the degree of removal is so great that the surface of the base is approached (penetration) is this noticeable in an abrupt rise in the production of carbon dioxide.

Thus mechanical roughening of the outer regions of the coating surface in the pyrolytic graphite already produces a considerable increase in reactivity. Further material removal given no further advantages quite apart from the fact that the protective effect of the pyrolytic graphite layers on the crucible is unnecessarily reduced. This applies particularly to removal of such large quantities that the effect of the preform material, i.e. the graphite, becomes noticeable.

To summarise, the graphite crucibles activated in accordance with the invention should be regarded in two lights:

(1) Activation by roughening, whereby a number of active centers is revealed, which number should not exceed a certain maximum.

(2) Activation by coating with a second, less oriented (sooty) carbon layer, whereby the reactivity is increased and in addition the reaction volume (the reactive mass) may be increased with the increasing thickness of this second layer.

The activated crucible of the invention may thus be produced by two methods, each with its characteristic features.

What is claimed is:

1. A method of making a crucible for flameless atomic absorption spectroscopy comprising the steps of:
   forming a carbon preform having a coating of pyrolytic graphite, and
   coating said pyrolytic graphite with a layer of carbon having a low degree of orientation, said layer having a crystalline orientation greatly differing from that of an ideal graphite lattice,
   said layer being applied by deposition from a gas phase.

2. A method according to claim 1, wherein said pyrolytic graphite coating is mechanically or chemically roughened before said step of coating.

3. A method of making a crucible for flameless atomic absorption spectroscopy comprising the steps of:
   forming a carbon preform having a coating of pyrolytic graphite,
   covering said pyrolytic graphite coating with an emulsion consisting of carbon and soot particles, a thermally decomposable emulsifier and a volatile solvent, and
   heating said preform until only carbon or soot particles remain.

4. A method according to claim 3, wherein said pyrolytic graphite coating is mechanically or chemically roughened before said step of covering.

* * * * *

UNITED STATES PATENT AND TRADEMARK OFFICE
CERTIFICATE OF CORRECTION

PATENT NO. : 4,367,246

DATED : January 4, 1983

INVENTOR(S) : BERNHARD LERSMACHER ET AL

It is certified that error appears in the above—identified patent and that said Letters Patent is hereby corrected as shown below:

Column 3, Line 51, change "CFD to --CVD--;
Line 58, change "about about" to --at about--.

Signed and Sealed this

Twenty-ninth Day of March 1983

[SEAL]

Attest:

GERALD J. MOSSINGHOFF

Attesting Officer

Commissioner of Patents and Trademarks